United States Patent
Rong et al.

(10) Patent No.: US 12,102,420 B2
(45) Date of Patent: Oct. 1, 2024

(54) DIRECT RF SIGNAL PROCESSING FOR HEART-RATE MONITORING USING UWB IMPULSE RADAR

(71) Applicant: Arizona Board of Regents on behalf of Arizona State University, Scottsdale, AZ (US)

(72) Inventors: Yu Rong, Phoenix, AZ (US); Daniel W. Bliss, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 555 days.

(21) Appl. No.: 17/277,596

(22) PCT Filed: Sep. 27, 2019

(86) PCT No.: PCT/US2019/053425
§ 371 (c)(1),
(2) Date: Mar. 18, 2021

(87) PCT Pub. No.: WO2020/072297
PCT Pub. Date: Apr. 9, 2020

(65) Prior Publication Data
US 2021/0353156 A1   Nov. 18, 2021

Related U.S. Application Data

(60) Provisional application No. 62/740,651, filed on Oct. 3, 2018.

(51) Int. Cl.
*A61B 5/024* (2006.01)
*A61B 5/00* (2006.01)
(Continued)

(52) U.S. Cl.
CPC ............ *A61B 5/024* (2013.01); *A61B 5/05* (2013.01); *A61B 5/0507* (2013.01);
(Continued)

(58) Field of Classification Search
None
See application file for complete search history.

(56) References Cited

U.S. PATENT DOCUMENTS 3,110,897 A   11/1963   Laurent
3,719,945 A    3/1973   Sletten et al.
(Continued)

FOREIGN PATENT DOCUMENTS

CN    106264501 A    1/2017
EP     3479140 A1    5/2019
(Continued)

OTHER PUBLICATIONS

Aoyagi, T. et al., "Pulse oximetry: Its invention, contribution to medicine, and future tasks," Anesthesia and Analgesia, vol. 94, Feb. 2002, 5 pages.
(Continued)

*Primary Examiner* — Jonathan Cwern
(74) *Attorney, Agent, or Firm* — Withrow & Terranova, P.L.L.C.; Vincent K. Gustafson

(57) ABSTRACT

Methods, systems, and devices for direct radio frequency (RF) signal processing for heart rate (HR) monitoring using ultra-wide band (UWB) impulse radar are presented. A radar sensor is able to directly sample a received signal at RF which satisfies the Nyquist sampling rate, preserving a subject's vital sign information in the received signal. The vital sign information can be extracted directly from a raw RF signal and thus down conversion to a complex baseband is not required. The HR monitoring performance from the proposed direct RF signal processing technique provides an
(Continued)

improvement in continuous HR monitoring as compared against existing methods using a complex baseband signal and/or other measurement techniques.

17 Claims, 7 Drawing Sheets

(51) Int. Cl.
 A61B 5/05 (2021.01)
 A61B 5/0507 (2021.01)
 G01S 13/02 (2006.01)
 G01S 13/524 (2006.01)
 G01S 13/88 (2006.01)
(52) U.S. Cl.
 CPC ........ *A61B 5/7207* (2013.01); *G01S 13/0209* (2013.01); *G01S 13/524* (2013.01); *G01S 13/88* (2013.01)

(56) References Cited

U.S. PATENT DOCUMENTS

| | | | |
|---|---|---|---|
| 4,803,489 A | 2/1989 | Giori | |
| 4,860,014 A | 8/1989 | Shores et al. | |
| 5,424,749 A | 6/1995 | Richmond | |
| 5,565,872 A | 10/1996 | Prevatt et al. | |
| 5,828,331 A | 10/1998 | Harper | |
| 6,026,340 A | 2/2000 | Corrado et al. | |
| 6,736,231 B2 | 5/2004 | Breed et al. | |
| 6,861,974 B1 | 3/2005 | Poe et al. | |
| 6,909,397 B1 | 6/2005 | Greneker, III et al. | |
| 7,567,200 B1 | 7/2009 | Osterweil | |
| 7,782,256 B2 | 8/2010 | Smith | |
| 7,916,066 B1 | 3/2011 | Osterweil | |
| 8,068,051 B1 | 11/2011 | Osterweil | |
| 8,454,528 B2 | 6/2013 | Yuen et al. | |
| 8,483,761 B2 | 7/2013 | Li et al. | |
| 8,681,585 B2 | 3/2014 | Dahl et al. | |
| 8,686,362 B2 | 4/2014 | Bakhtiari et al. | |
| 8,687,689 B2 | 4/2014 | Baraniuk et al. | |
| 8,712,069 B1 | 4/2014 | Murgia et al. | |
| 9,164,167 B2 | 10/2015 | Hyde et al. | |
| 9,200,945 B2 | 12/2015 | Lin et al. | |
| 9,297,886 B1 | 3/2016 | Mountcastle et al. | |
| 9,329,728 B2 | 5/2016 | Dahl | |
| 9,341,706 B2 | 5/2016 | Ward | |
| 9,357,293 B2 | 5/2016 | Claussen | |
| 9,568,595 B2 | 2/2017 | Zack et al. | |
| 9,737,219 B2 | 8/2017 | Chen | |
| 9,775,520 B2 | 10/2017 | Tran | |
| 9,971,027 B1 | 5/2018 | Stockmann et al. | |
| 10,019,998 B2 | 7/2018 | Bilobrov et al. | |
| 10,042,038 B1 | 8/2018 | Lord | |
| 10,063,965 B2 | 8/2018 | Kim et al. | |
| 10,078,328 B1 | 9/2018 | Slater | |
| 10,197,667 B2 | 2/2019 | Reil et al. | |
| 10,201,278 B2 | 2/2019 | Lux et al. | |
| 10,209,825 B2 | 2/2019 | Sheng et al. | |
| 10,228,449 B2 | 3/2019 | Nguyen et al. | |
| 10,234,543 B2 | 3/2019 | Mazzaro et al. | |
| 10,234,552 B1 | 3/2019 | Jazayeri et al. | |
| 10,310,073 B1 | 6/2019 | Santra et al. | |
| 10,436,888 B2 | 10/2019 | Li et al. | |
| 10,481,245 B2 | 11/2019 | LaPat et al. | |
| 10,753,727 B2 | 8/2020 | Klose et al. | |
| 10,918,287 B2 | 2/2021 | Islam | |
| 10,928,374 B2 | 2/2021 | Islam | |
| 10,955,524 B2 | 3/2021 | Crane et al. | |
| 11,051,702 B2 | 7/2021 | Lin et al. | |
| 11,240,579 B2 | 2/2022 | Jumbe et al. | |
| 11,624,821 B2 | 4/2023 | Rappaport | |
| 2005/0024257 A1 | 2/2005 | Britton et al. | |
| 2005/0128123 A1 | 6/2005 | Greneker, III et al. | |
| 2005/0168336 A1 | 8/2005 | Donskoy et al. | |
| 2006/0054438 A1 | 3/2006 | Asaba et al. | |
| 2006/0253278 A1 | 11/2006 | Furst-Yust et al. | |
| 2008/0077015 A1 | 3/2008 | Boric-Lubecke et al. | |
| 2008/0135762 A1 | 6/2008 | Villanucci et al. | |
| 2008/0151694 A1 | 6/2008 | Slater | |
| 2008/0214903 A1 | 9/2008 | Orbach | |
| 2009/0135086 A1 | 5/2009 | Fuller et al. | |
| 2009/0203972 A1 | 8/2009 | Heneghan et al. | |
| 2010/0011845 A1 | 1/2010 | Laughard, Jr. et al. | |
| 2010/0130873 A1 | 5/2010 | Yuen et al. | |
| 2010/0152600 A1* | 6/2010 | Droitcour | A61B 5/1113 600/534 |
| 2010/0290063 A1 | 11/2010 | Bakhtiari et al. | |
| 2011/0102247 A1 | 5/2011 | Pauli et al. | |
| 2012/0022348 A1 | 1/2012 | Droitcour et al. | |
| 2012/0232388 A1 | 9/2012 | Curra et al. | |
| 2013/0030257 A1 | 1/2013 | Nakata et al. | |
| 2013/0053653 A1 | 2/2013 | Cuddihy et al. | |
| 2013/0300473 A1 | 11/2013 | Bass et al. | |
| 2013/0300573 A1* | 11/2013 | Brown | G01S 13/42 340/870.01 |
| 2014/0024917 A1 | 1/2014 | McMahon et al. | |
| 2014/0128748 A1 | 5/2014 | Horng et al. | |
| 2014/0194793 A1 | 7/2014 | Nakata et al. | |
| 2014/0212986 A1 | 7/2014 | Angelescu et al. | |
| 2014/0276089 A1 | 9/2014 | Kirenko et al. | |
| 2014/0276099 A1 | 9/2014 | Kirenko et al. | |
| 2014/0276104 A1 | 9/2014 | Tao et al. | |
| 2014/0312986 A1 | 10/2014 | Edelstein et al. | |
| 2014/0378809 A1* | 12/2014 | Weitnauer | A61B 5/24 600/407 |
| 2015/0223733 A1 | 8/2015 | Al-Alusi | |
| 2015/0241555 A1 | 8/2015 | Lin et al. | |
| 2015/0319540 A1 | 11/2015 | Rubinstein et al. | |
| 2015/0342535 A1 | 12/2015 | Chen | |
| 2015/0379370 A1 | 12/2015 | Clifton et al. | |
| 2016/0022204 A1 | 1/2016 | Mostov | |
| 2016/0054438 A1 | 2/2016 | Patole et al. | |
| 2016/0089052 A1 | 3/2016 | Cho et al. | |
| 2016/0188831 A1 | 6/2016 | Kurtz et al. | |
| 2016/0274218 A1 | 9/2016 | McCaughey et al. | |
| 2016/0287208 A1 | 10/2016 | Zhai | |
| 2017/0042432 A1 | 2/2017 | Adib et al. | |
| 2017/0131335 A1 | 5/2017 | Pratt et al. | |
| 2017/0173262 A1 | 6/2017 | Veltz | |
| 2017/0174343 A1 | 6/2017 | Erickson et al. | |
| 2017/0341745 A1 | 11/2017 | Sekine et al. | |
| 2018/0000408 A1 | 1/2018 | Heinrich et al. | |
| 2018/0049669 A1 | 2/2018 | Vu et al. | |
| 2018/0085009 A1 | 3/2018 | Aiello et al. | |
| 2018/0085013 A1 | 3/2018 | Cho et al. | |
| 2018/0263502 A1 | 9/2018 | Lin et al. | |
| 2018/0289305 A1 | 10/2018 | Rahman et al. | |
| 2019/0059746 A1 | 2/2019 | McMahon et al. | |
| 2019/0064364 A1 | 2/2019 | Boysel et al. | |
| 2019/0077007 A1 | 3/2019 | Mallinson | |
| 2019/0142289 A1 | 5/2019 | Bliss et al. | |
| 2019/0240535 A1 | 8/2019 | Santra et al. | |
| 2020/0025876 A1 | 1/2020 | Chuang et al. | |
| 2020/0037890 A1 | 2/2020 | Cho et al. | |
| 2020/0196866 A1 | 6/2020 | Chiou et al. | |
| 2020/0271749 A1 | 8/2020 | Wu et al. | |
| 2020/0297227 A1 | 9/2020 | Rong et al. | |
| 2020/0302609 A1 | 9/2020 | Rong et al. | |
| 2021/0018610 A1 | 1/2021 | Babakhani et al. | |
| 2021/0093203 A1 | 4/2021 | Zhong et al. | |
| 2022/0142478 A1 | 5/2022 | Bliss et al. | |
| 2022/0373646 A1 | 11/2022 | Nguyen et al. | |
| 2023/0000396 A1 | 1/2023 | Coffey et al. | |

FOREIGN PATENT DOCUMENTS

| | | |
|---|---|---|
| EP | 3739356 A1 | 11/2020 |
| EP | 4162865 A1 | 4/2023 |
| JP | 2022153626 A | 10/2022 |
| WO | 0116554 A2 | 3/2001 |
| WO | 0116554 A3 | 9/2001 |
| WO | 2005091014 A1 | 9/2005 |
| WO | 2008001092 A2 | 1/2008 |

(56) References Cited

FOREIGN PATENT DOCUMENTS

| WO | 2009009690 A2 | 1/2009 |
|---|---|---|
| WO | 2012055148 A1 | 5/2012 |
| WO | 2013027027 A2 | 2/2013 |
| WO | 2016185004 A1 | 11/2016 |
| WO | 2017180985 A1 | 10/2017 |
| WO | 2018050913 A1 | 3/2018 |
| WO | 2018213757 A1 | 11/2018 |
| WO | 2018234394 A1 | 12/2018 |
| WO | 2020072297 A1 | 4/2020 |
| WO | 2020191142 A1 | 9/2020 |
| WO | 2021202677 A1 | 10/2021 |

OTHER PUBLICATIONS

Benton, C. et al., "Terahertz Radar for Remote Measurement of Vital Signs," 2008 Joint Meeting of the APS Ohio-Region Section, the AAPT Southern Ohio Section, and the ACS Dayton-Section, Oct. 10-11, 2008, Dayton, Ohio, American Physical Society, Abstract only, 1 page.
Rong, Y. et al., "Respiration and Cardiac Activity Sensing Using 3-D Cameras," 2020 54th Asilomar Conference on Signals, Systems, and Computers, Nov. 1-4, 2020, Pacific Grove, CA, USA, IEEE, 5 pages.
Theofanopoulos, P.C. et al., "A Novel Fingerprint Scanning Method Using Terahertz Imaging, " 2018 IEEE International Symposium on Antennas and Propagation & USNC/URSI National Radio Science Meeting, Jul. 8-13, 2018, Boston, MA, USA, IEEE, 2 pages.
Jensen, J. et al., "Camera-based Heart Rate Monitoring," B.Sc. Thesis, Bachelor of Science in Engineering, Department of Applied Mathematics and Computer Science, Technical University of Denmark, 2014, 72 pages.
Unakafov, A., "Pulse rate estimation usinG imaging photoplethysmography: generic framework and comparison of methods on a publicly available dataset," arXiv:1710.08369v1 [eess.IV], Oct. 17, 2017, 17 pages.
Non-Final Office Action for U.S. Appl. No. 16/823,587, mailed Oct. 24, 2022, 26 pages.
Extended European Search Report for European Patent Application No. 20772680.3, mailed Nov. 8, 2022, 8 pages.
Ahmad, A. et al., "Vital signs monitoring of multiple people using a FMCW millimeter-wave sensor," 2018 IEEE Radar Conference (RadarConf18), Apr. 23-27, 2018, Oklahoma City, OK, USA, IEEE, 6 pages.
Alizadeh, M. et al., "Remote Monitoring of Human Vital Signs Using mm-Wave FMCW Radar," IEEE Access, vol. 7, Apr. 2019, IEEE, 12 pages.
Al-Naji, A. et al., "Remote Optical Cardiopulmonary Signal Extraction With Noise Artifact Removal, Multiple Subject Detection & Long-Distance," IEEE Access, vol. 6, 2018, IEEE, pp. 11573-11595.
Anderson, R. et al., "The Optics of Human Skin," Journal of Investigative Dermatology, vol. 77, Issue 1, Jul. 1981, Elsevier, pp. 13-19.
Allen, J., "Photoplethysmography and its application in clinical physiological measurement," Physiological Measurement, vol. 28, No. 3, Feb. 2007, IOP Publishing, 40 pages.
Author Uknown, "Apple Watch Series 5," accessed Nov. 16, 2018 from https://www.apple.com/apple-watch-series-4/health/, 13 pages.
Author Uknown, "Shimmer3 ECG Unit," accessed Nov. 16, 2018 from http://www.shimmersensing.com/products/shimmer3-ecg-sensor, 6 pages.
Biswas, D. et al., "Heart Rate Estimation From Wrist-Worn Photoplethysmography: A Review," IEEE Sensors Journal, vol. 19, Issue 16, Aug. 2019, IEEE, pp. 6560-6570.
Chen, K.-M. et al., "An X-Band Microwave Life-Detection System," IEEE Transactions on Biomedical Engineering, vol. BME-33, Issue 7, Jul. 1986, IEEE, 5 pages.
Chen, V.C. et al., "Micro-Doppler effect in radar: phenomenon, model, and simulation study," IEEE Transactions on Aerospace and Electronic Systems, vol. 42, Issue 1, Jan. 2006, IEEE, 20 pages.
Chen, K-M. et al., "Microwave life-detection systems for searching human subjects under earthquake rubble or behind barrier," IEEE Transactions on Biomedical Engineering, vol. 47, Issue 1, Jan. 2000, IEEE, pp. 105-114.
Chen, V. et al., "Time-Frequency Transforms for Radar Imaging and Signal Analysis," Artech House, 2002, 233 pages.
Churkin, S. et al., "Millimeter-wave radar for vital signs monitoring," 2015 IEEE International Conference on Microwaves, Communications, Antennas and Electronic Systems (COMCAS), Nov. 2-4, 2015, Tel Aviv, Israel, IEEE, 4 pages.
Damianou, D., "The wavelength dependence of the photoplethysmogram and its implication to pulse oximetry," Ph. D. Thesis, University of Nottingham, 1995, 223 pages.
Davila, M. et al., "The PhysioCam: Cardiac Pulse, Continuously Monitored by a Color Video Camera," Journal of Medical Devices, vol. 10, Issue 2, Jun. 2016, published online May 2016, 2 pages.
Doerry, A., "Just Where Exactly is the Radar? (a.k.a. The Radar Antenna Phase Center)," Sandia Report SAND2013-10635, Dec. 2013, Sandia National Laboratories, 26 pages.
Esteep, J. et al., "Recovering Pulse Rate During Motion Artifact with a Multi-Imager Array for Non-Contact Imaging Photoplethysmography," 2014 IEEE International Conference on Systems, Man, and Cybernetics, Oct. 5-8, 2014, San Diego, CA, USA, 8 pages.
Fallow, B.A. et al., "Influence of skin type and wavelength on light wave reflectance," Journal of Clinical Monitoring and Computing, vol. 27, No. 3, Feb. 2013, 7 pages.
Fathy, Ramzie, et al., "Comparison of UWB Doppler radar and Camera based Photoplethysmography in Non-contact Multiple Heartbeats Detection," BioWireleSS, 2016, IEEE, pp. 25-28.
Feldman, Y. et al., "The electromagnetic response of human skin in the millimetre and submillimetre wave range," Physics in Medicine and Biology, vol. 54(11), Jul. 2009, 25 pages.
Feng, Litong, et al., "Motion-Resistant Remote Imaging Photoplethysmography Based on the Optical Properties of Skin," IEEE Transactions on Circuits and Systems for Video Technology, vol. 25, Issue 5, May 2015, pp. 879-891.
Fitzpatrick, T., "The validity and practicality of sun-reactive skin types I through VI," Archives of Dermatology, vol. 124, No. 6, Jun. 1988, pp. 869-871.
Fox, K. et al., "Resting Heart Rate in Cardiovascular Disease," Journal of the American College of Cardiology, vol. 50, No. 9, 2007, Elsevier Inc., pp. 823-830.
Gu, C. et al., "A Hybrid Radar-Camera Sensing System With Phase Compensation for Random Body Movement Cancellation in Doppler Vital Sign Detection," IEEE Transactions on Microwave Theory and Techniques, vol. 61, Issue 12, Dec. 2013, first published Nov. 2013, IEEE, 12 pages.
Hayut, I. et al., "The Helical Structure of Sweat Ducts: Their Influence on the Electromagnetic Reflection Spectrum of the Skin," IEEE Transactions on Terahertz Science and Technology, vol. 3, Issue 2, Mar. 2013, first published Dec. 2012, IEEE, 10 pages.
Holmes, G. et al., "Generating Rule Sets from Model Trees, " 12th Australian Joint Conference on Artificial Intelligence, Dec. 1999, 9 pages.
Humphreys, K. et al., "Noncontact simultaneous dual wavelength photoplethysmography: a further step toward honcontact pulse oximetry," Review of Scientific Instruments, vol. 78, Issue 4, Apr. 2007, AIP Publishing, 7 pages.
It's Foundation, "Overview—Database of Tissue Properties," 2010-2022, accessed Aug. 31, 2014 from https://itis.swiss/virtual-population/tissue-properties/database/database-summary/, 2 pages.
Kamal, A. et al., "Skin photoplethysmography-a review," Computer Methods and Programs in Biomedicine, vol. 28, No. 4, Apr. 1989, pp. 257-269.
Kamshilin, A. et al., A new look at the essence of the imaging photoplethysmography, Scientific Reports, vol. 5:10494, , May 2015, 9 pages.

(56) References Cited

OTHER PUBLICATIONS

Kebe, M. et al., "Human Vital Signs Detection Methods and Potential Using Radars: A Review," Sensors, vol. 20, Mar. 2020, MDPI, 38 pages.

Klemm, M. et al., "Breast Cancer Detection using Symmetrical Antenna Array," The Second European Conference on Antennas and Propagation, EuCAP 2007, Nov. 11-16, 2007, Edinburgh, IET, 5 pages.

Laman, N. et al., "High-Resolution Waveguide THz Spectroscopy of Biological Molecules," Biophysical Journal, vol. 94, Issue 3, Feb. 2008, pp. 1010-1020.

Li, Changzhi, "Doppler Phase Modulation Effect for Non-contact Accurate Measurement of Vital Signs and other Periodic Movements—From Theory to CMOS System on Chip Integrations," A Dissertation presented to the Graduate School of the University of Florida, 2009, 129 pages.

Li, C. et al., "Experiment and Spectral Analysis of a Low-Power Ka-Band Heartbeat Detector Measuring From Four Sides of a Human Body," IEEE Transactions on Microwave Theory and Techniques, vol. 54, Issue 12, Dec. 2006, IEEE, 9 pages.

Li, C. et al., "Random Body Movement Cancellation in Doppler Radar Vital Sign Detection," IEEE Transactions on Microwave Theory and Techniques, vol. 56, Issue 12, Dec. 2008, first published Nov. 18, 2008, IEEE, 4 pages.

Lin, J., "Noninvasive Microwave Measurement of Respiration," Proceedings of the IEEE, vol. 63, Issue 10, Oct. 1975, IEEE, 1 page.

Noon, D.A., "Stepped-Frequency Radar Design and Signal Processing EnhancesGround Penetrating Radar Performance," A thesis submitted for the degree of Doctor of Philosophy (PhD) of The University of Queensland, Jan. 1996, 186 pages.

Nowara, E. et al., "PPGSecure: Biometric Presentation Attack Detection Using Photopletysmograms," 12th IEEE International Conference on Automatic Face & Gesture Recognition (FG 2017), May 30-Jun. 3, 2017, Washington, DC, USA, IEEE, 3 pages.

Nowara, E. et al., "SparsePPG: Towards Driver Monitoring Using Camera-Based Vital Signs Estimation in Near-Infrared," 2018 IEEE/CVF Conference on Computer Vision and Pattern Recognition Workshops (CVPRW), Jun. 18-22, 2018, Salt Lake City, UT, USA, IEEE, 10 pages.

O'Brien, S., "Deepfakes are coming. Is Big Tech ready?" CNN Money, Aug. 8, 2018, 3 pages.

Orfanidis, S. J, "Electromagnetic Waves and Antennas," 2002, Rutgers University, 547 pages.

Petkie, D. et al., "Remote respiration and heart rate monitoring with millimeter-wave/terahertz radars," Proceedings of SPIE, vol. 7117, Oct. 2008, 6 pages.

Petkie, D et al., "Millimeter-Wave Radar for Vital Signs Sensing," Radar Sensor Technology XIII Conference, Apr. 13-15, 2009, Orlando, FL, 5 pages.

Poh, M.-Z. et al., "Advancements in Noncontact, Multiparameter Physiological Measurements Using a Webcam," IEEE Transactions on Biomedical Engineering, vol. 58, Issue 1, Jan. 2011, Oct. 14, 2010, IEEE, 5 pages.

Poh, Ming-Zher, et al., "Non-contact, automated cardiac pulse measurements using video imaging and blind sourceseparation," Optics Express, vol. 18, Issue 10, May 2010, 13 pages.

Quinlan, R., "Learning with Continuous Classes," 5th Australian Joint Conference on Artifical Intelligence, Nov. 1992, 6 pages.

Rahman, H. et al., "Real Time Heart Rate Monitoring from Facial RGB Color Video using Webcam," 9th Annual Workshop of the Swedish Artificial Intelligence Society (SAIS), May 2016, 9 pages.

Reid, C. et al., "Terahertz Time-Domain Spectroscopy of Human Blood," IEEE Journal of Biomedical and Health Informatics, vol. 17, Issue 4, Jul. 2013, first published Apr. 2013, IEEE, 11 pages.

Rong, Y. et al., "Active Breathing Suppression for Improved Sleep Monitoring Heartbeat Detection Using UWB Radar," 2019 IEEE 8th International Workshop on Computational Advances in Multi-Sensor Adaptive Processing (CAMSAP), Dec. 15-18, 2019, IEEE, 5 pages.

Ma, Y. et al., "Speech Recovery Based On Auditory Radar and Webcam," 2019 IEEE MTT-S International Microwave Biomedical Conference (IMBioC), May 6-8, 2019, Nanjing, China, IEEE, 3 pages.

Extended European Search Report for European Patent Application No. 20882810.3, mailed Nov. 22, 2022, 9 pages.

Anderson, N. et al., "A 118-mW Pulse-Based Radar SoC in 55-nm CMOS for Non-Contact Human Vital Signs Detection," IEEE Journal of Solid-State Circuits, vol. 52, No. 12, Dec. 2017, IEEE, pp. 3421-3432.

Aumann, H.M. et al., "Doppler radar microphone with logarithmic square-law detector," Electronics Letters, vol. 52, No. 12, Jun. 2016, pp. 1061-1063.

Avargel, Y. et al., "Speech measurements using a laser Doppler vibrometer sensor: Application to speech enhancement," 2011 Joint Workshop on Hands-free Speech Communication and Microphone Arrays, May 30-Jun. 1, 2011, Edinburgh, UK, IEEE.

Chazal, P. et al., "Sleep/wake measurement using a noncontact biomotion sensor," Journal of Sleep Research, vol. 20, No. 2, Aug. 2010, pp. 356-366.

Chernov, N. et al., "Least Squares Fitting of Circles," Journal of Mathematical Imaging and Vision, vol. 23, No. 3, Nov. 2005, pp. 239-252.

Chung, K-Y. et al., "Noncontact Sleep Study by Multi-Modal Sensor Fusion," Sensors, vol. 17, No. 7, Jul. 2017, MDPI, 17 pages.

Davis, A. et al., "The Visual Microphone: Passive Recovery of Sound from Video," ACM Transactions on Graphics, vol. 33, No. 4, Jul. 2014, 10 pages.

Guan, S. et al., "Automated DC Offset Calibration Strategy for Structural Health Monitoring Based on Portable CW Radar Sensor," IEEE Transactions on Instrumentation and Measurement, vol. 63, No. 12, Dec. 2014, IEEE, pp. 3111-3118.

Geisheimer, J.L. et al., "A Surface Vibration Electromagnetic Speech Sensor," Multi-modal Speech Recognition Workshop 2002, Jun. 2002, Georgia Tech Research Institute, Atlanta Sensors and Electromagnetic Applications Lab, 5 pages.

Immoreev, I. et al., "UWB Radar for Patient Monitoring," IEEE Aerospace and Electronic Systems Magazine, vol. 23, Issue 11, Nov. 2008, IEEE, 8 pages.

Jiao, M. et al., "A Novel Radar Sensor for the Non-Contact Detection of Speech Signals," Sensors, vol. 10, No. 5, May 2010, pp. 4622-4633.

Lazaro, A. et al., "Analysis of Vital Signs Monitoring Using an IR-UWB Radar," Progress In Electromagnetics Research, vol. 100, Jan. 2010, pp. 265-284.

Lee, J.-M. et al., "Comparison of Wearable Trackers' Ability to Estimate Sleep," International Journal of Environmental Research and Public Health, vol. 15, No. 6, Jun. 2018, MDPI, 13 pages.

Li, C. et al., "Complex Signal Demodulation and Random Body Movement Cancellation Techniques for Non-contact Vital Sign Detection," 2008 IEEE MTT-S International Microwave Symposium Digest, Jun. 15-20, 2008, Atlanta, GA, USA, IEEE, 4 pages.

Mercuri, M. et al., "Vital-sign monitoring and spatial tracking of multiple people using a contactless radar-based sensor," Nature Electronics, vol. 2, Jun. 2019, pp. 252-262.

Nam, Y. et al., "Sleep Monitoring Based on a Tri-Axial Accelerometer and a Pressure Sensor," Sensors, vol. 16, No. 5, May 2016, MDPI, 14 pages.

Park, B.-K. et al., "Arctangent Demodulation With DC Offset Compensation in Quadrature Doppler Radar Receiver Systems," IEEE Transactions on Microwave Theory and Techniques, vol. 55, No. 5, May 2007, IEEE, pp. 1073-1079.

Rahmati, M. et al., "SSFB: Signal-Space-Frequency Beamforming for Underwater Acoustic Video Transmission," 2017 IEEE 14th International Conference on Mobile Ad Hoc and Sensor Systems (MASS), Oct. 22-25, 2017, Orlando, FL, USA, IEEE, pp. 180-188.

Ren, L. et al., "Noncontact Heartbeat Detection using UWB Impulse Doppler Radar," 2015 IEEE Topical Conference on Biomedical Wireless Technologies, Networks, and Sensing Systems (BioWireleSS), Jan. 25-28, 2015, San Diego, CA, IEEE, 3 pages.

(56) References Cited

OTHER PUBLICATIONS

Ren, L. et al., "Phase-Based Methods for Heart Rate Detection Using UWB Impulse Doppler Radar," IEEE Transactions on Microwave Theory and Techniques, vol. 64, Issue 10, Oct. 2016, IEEE, 13 pages.

Rong, Y. et al., "Harmonics-Based Multiple Heartbeat Detection at Equal Distance using UWB Impulse Radar," 2018 IEEE Radar Conference (RadarConf18), Apr. 23-27, 2018, Oklahoma City, OK, USA, IEEE, 5 pages.

Rong, Y. et al., "Remote Sensing for Vital Information Based on Spectral-Domain Harmonic Signatures," IEEE Transactions on Aerospace and Electronic Systems, vol. 55, No. 6, May 2019, IEEE, 12 pages.

Rong, Y. "Remote Sensing For Vital Signs Monitoring Using Advanced Radar Signal Processing Techniques," A Dissertation Presented in Partial Fulfillment of the Requirements for the Degree Doctor of Philosophy, Arizona State University, Dec. 2018, 117 pages.

Rong, Y. et al., "Smart Homes: See Multiple Heartbeats Through Wall Using Wireless Signals," 2019 Radar Conference (RadarConf), Apr. 2019, Boston, MA, USA, IEEE, 6 pages.

Rothberg, S. et al., "Laser vibrometry: Pseudo-vibrations," Journal of Sound and Vibration, Dec. 1989, Elsevier, 18 pages.

Savage, H.O. et al., "Development and validation of a novel non-contact monitor of nocturnal respiration for Identifying sleep-disordered breathing in patients with heart failure," ESC Heart Failure, vol. 3, No. 3, Sep. 2016, John Wiley & Sons, pp. 212-219.

Staderini, E.M., "UWB Radars in Medicine," IEEE Aerospace and Electronic Systems Magazine, vol. 17, No. 1, Feb. 2002, pp. 13-18.

Tian, Y. et al., "Smart radar sensor for speech detection and enhancement," Sensors and Actuators A: Physical, vol. 191, Mar. 2013, Elsevier, pp. 99-104.

Viswanathan, V. et al., "Noise-immune multisensor speech input: formal subjective testing in operational conditions," International Conference on Acoustics, Speech, and Signal Processing, May 23-26, 1989, Glasgow, UK, IEEE, pp. 373-376.

Viswanathan, V. et al., "Noise-immune speech transduction using multiple sensors," IEEE International Conference on Acoustics, Speech, and Signal Processing (ICASSP'85), Apr. 26-29, 1985, Tampa, FL, USA, IEEE, 4 pages.

Yacchirema, D.C., "A Smart System for Sleep Monitoring by Integrating IoT With Big Data Analytics," IEEE Access, vol. 6, Jun. 2018, 16 pages.

Zhao, H et al., "A Portable 24-GHz Auditory Radar for Non-contact Speech Sensing with Background Noise Rejection and Directional Discrimination," 2016 IEEE MTT-S International Microwave Symposium (IMS), May 22-27, 2016, San Francisco, CA, USA, IEEE, 4 pages.

Invitation to Pay Additional Fees for International Patent Application No. PCT/US2019/053425, mailed Nov. 27, 2019, 2 pages.

International Search Report and Written Opinion for International Patent Application No. PCT/US2019/053425, mailed Jan. 30, 2020, 10 pages.

International Preliminary Report on Patentability for International Patent Application No. PCT/US2019/053425, mailed Apr. 15, 2021, 7 pages.

International Search Report and Written Opinion for International Patent Application No. PCT/US2020/057452, mailed Feb. 12, 2021, 11 pages.

International Search Report and Written Opinion for International Patent Application No. PCT/US2020/058326, mailed Feb. 3, 2021, 13 pages.

Al-Naji, A. et al., "Remote measurement of cardiopulmonary signal using an unmanned aerial vehicle," IOP Conference Series: Materials Science and Engineering, vol. 405, Sep. 2018, IOP Publishing, 10 pages.

Final Office Action and Examiner-Initiated Interview Summary for U.S. Appl. No. 16/823,587, mailed Mar. 2, 2023, 25 pages.

Non-Final Office Action for U.S. Appl. No. 16/823,599, mailed Feb. 1, 2023, 13 pages.

Author Unknown, "XeThru X4," available as early as Apr. 40, 2019, accessed Jun. 9, 2022 from https://www.radartutorial.eu/19.kartei/13.labs/karte009.en.html, 1 page.

Lee, J. et al., "Sleep Monitoring System Using Kinect Sensor," International Journal of Distributed Sensor Networks, vol. 11, No. 10, Oct. 2015, Hindawi Publishing Corporation, 10 pages.

Notice of Allowance for U.S. Appl. No. 17/772,844, mailed Feb. 23, 2023, 9 pages.

Non-Final Office Action for U.S. Appl. No. 17/773,503, mailed Mar. 14, 2023, 23 pages.

Advisory Action, Examiner-Initiated Interview Summary, and AFCP 2.0 Decision for U.S. Appl. No. 16/823,587, mailed May 4, 2023, 5 pages.

Notice of Allowance for U.S. Appl. No. 16/823,587, mailed May 26, 2023, 10 pages.

Notice of Allowance and Examiner-Initiated Interview Summary for U.S. Appl. No. 16/823,599, mailed May 31, 2023, 10 pages.

Final Office Action for U.S. Appl. No. 17/773,503, mailed Aug. 10, 2023, 22 pages.

Rong, Y. et al., "Cardiac Sensing Exploiting an Ultra-Wideband Terahertz Sensing System," 2020 IEEE International Radar Conference (RADAR), Apr. 28-30, 2020, Washington, DC, USA, IEEE, 5 pages.

Rong, Y. et al., "Direct RF Signal Processing For Heart-Rate Monitoring Using UWB Impulse Radar," 2018 52nd Asilomar Conference on Signals, Systems, and Computers, Oct. 28-31, 2018, Pacific Grove, CA, IEEE, pp. 1215-1219.

Rong, Y. et al., "Is Radar Cardiography (RCG) Possible?," 2019 IEEE Radar Conference (RadarConf), Apr. 22-26, 2019, Boston, MA, USA, IEEE, 6 pages.

Rong, Y. et al., "Multiple source detection performance of linear sparse arrays," 2016 50th Asilomar Conference on Signals, Systems and Computers, Nov. 6-9, 2016, Pacific Grove, CA, USA, IEEE, 5 pages.

Rong, Y. et al., "Non-Contact Vital Signs Detection with UAV-Borne Radars," arXiv:2011.13982v1 [eess.SP], Nov. 27, 2020, 7 pages.

Rong, Y. et al., "Remote Sensing for Vital Information Based on Spectral-Domain Harmonic Signatures," IEEE Transactions on Aerospace and Electronic Systems, vol. 55, No. 6, Dec. 2019, OAPA, pp. 3454-3465.

Rong, Y. et al., "Smart Homes: See Multiple Heartbeats Through Wall Using Wireless Signals," 2019 IEEE Radar Conference (RadarConf), Apr. 22-26, 2019, Boston, MA, USA, IEEE, 6 pages.

Singh, A. et al., "Data-Based Quadrature Imbalance Compensation for a CW Doppler Radar System," IEEE Transactions on Microwave Theory and Techniques, vol. 61, No. 4, Apr. 2013, IEEE, pp. 1718-1724.

Spetlik, R. et al., "Non-Contact Reflectance Photoplethysmography: Progress, Limitations, and Myths," 2018 13th IEEE International Conference on Automatic Face & Gesture Recognition (FG 2018), May 15-19, 2018, IEEE, 8 pages.

Sun, Y. et al., "Noncontact imaging photoplethysmography to effectively access pulse rate variability," Journal of Biomedical Optics, vol. 18, No. 6, Jun. 2013, 10 pages.

Tang, M.-C. et al., "A Self- and Mutually Injection-Locked Radar System for Monitoring Vital Signs in Real Time With Random Body Movement Cancellation," IEEE Transactions on Microwave Theory and Techniques, vol. 64, Issue 12, Dec. 2016, first published Nov. 2016, IEEE, 11 pages.

Tang, M.-C. et al., "Single Self-Injection-Locked Radar With Two Antennas for Monitoring Vital Signs With Large Body Movement Cancellation," IEEE Transactions on Microwave Theory and Techniques, vol. 65, Issue 12, Dec. 2017, first published Nov. 2017, IEEE, 10 pages.

Theofanopoulos, P.C. et al., "A Terahertz Microscopy Technique for Sweat Duct Detection," 2018 IEEE/MTT-S International Microwave Symposium—IMS, Jun. 10-15, 2018, Philadelphia, PA, USA, IEEE, 4 pages.

Tripathi, S. et al., "Morphology of human sweat ducts observed by optical coherencetomography and their frequency of resonance in the terahertz frequency region," Scientific Reports, vol. 5, Article No. 9071, Mar. 2015, 7 pages.

(56) References Cited

OTHER PUBLICATIONS

Verkruysse, W. et al., "Remote plethysmographic imaging using ambient light," Optics Express, vol. 16, No. 26, Dec. 2008, 16 pages.

Wang, F.-K. et al., "Detection of Concealed Individuals Based on Their Vital Signs by Using a See-Through-Wall Imaging System With a Self-Injection-Locked Radar," IEEE Transactions on Microwave Theory and Techniques, vol. 61, Issue 1, Jan. 2013, Dec. 2012, IEEE, 9 pages.

Wang, S. et al., "A Novel Ultra-Wideband 80 GHz FMCW Radar System for Contactless Monitoring of Vital Signs," 2015 37th Annual International Conference of the IEEE Engineering in Medicine and Biology Society (EMBC), Aug. 25-29, 2015, Milan, Italy, IEEE, pp. 4978-4981.

Wang, W. et al., "Unsupervised Subject Detection via Remote-PPG," IEEE Transactions on Biomedical Engineering, vol. 62, No. 11, Nov. 2015, first published Jun. 2015, IEEE, 9 pages.

Wang, Y. et al., "Induction of model trees for predicting continuous classes," Proceedings of the poster papers of the 9th European Conference on Machine Learning, Apr. 1997, 12 pages.

Wiede, C. et al., "Remote Heart Rate Determination in RGB Data," Proceedings of the 5th International Conference on Pattern Recognition Applications and Methods (ICPRAM 2016), Feb. 2016, SCITEPRESS, pp. 240-246.

Wolff, C., "Organ-Pipe Scanner," accessed Feb. 2019 from https://www.radartutorial.eu/06.antennas/an66.en.html, 1 page.

Yan, Jiaming, et al., "Through-WallMultiple Targets Vital Signs Tracking Based on VMD Algorithm," Sensors, vol. 16, Issue 8, Aug. 2016, 11 pages.

Youseph, S. et al., "Pixel and Edge Based Illuminant Color Estimation for Image Forgery Detection," Procedia Computer Science, vol. 46, Oct. 2015, Elsevier B.V., 8 pages.

Yu et al., "Heart Rate Estimation from Facial Images using Filter Bank," 2014 6th International Symposium on Communications, Control and Signal Processing (ISCCSP), May 21-23, 2014, Athens, Greece, IEEE, 4 pages.

Zhang, Q. et al., "Heart Rate Extraction Based on Near-Infrared Camera: Towards Driver State Monitoring, " IEEE Access, vol. 6, Jun. 2018, IEEE, 11 pages.

Zhu et al., "Doppler Radar Techniques for Vital Signs Detection Featuring Noise Cancellations," 2019 IEEE MTT-S Interational Microwave Biomedical Conference, May 2019, IEEE, 6 pages.

Non-Final Office Action for U.S. Appl. No. 16/823,587, mailed Nov. 23, 2021, 19 pages.

Final Office Action for U.S. Appl. No. 16/823,587, mailed May 25, 2022, 34 pages.

International Search Report and Written Opinion for International Patent Application No. PCT/US2020/023533, mailed Jun. 18, 2020, 11 pages.

International Search Report and Written Opinion for International Patent Application No. PCT/US2021/025106, mailed Jul. 20, 2021, 10 pages.

Advisory Action for U.S. Appl. No. 17/773,503, mailed Nov. 9, 2023, 3 pages.

Applicant-Initiated Interview Summary for U.S. Appl. No. 17/773,503, mailed Dec. 11, 2023, 2 pages.

Notice of Allowance for U.S. Appl. No. 17/773,503, mailed Jan. 18, 2024, 17 pages.

Non-Final Office Action for U.S. Appl. No. 17/435,580, mailed Jul. 30, 2024, 11 pages.

\* cited by examiner

DIRECT RF SIGNAL PROCESSING FOR HEART-RATE MONITORING USING UWB IMPULSE RADAR

This application is a 35 USC 371 national phase filing of International Application No. PCT/US2019/053425, filed Sep. 27, 2019, the disclosure of which is incorporated herein by reference in its entirety.

RELATED APPLICATIONS

This application claims the benefit of provisional patent application Ser. No. 62/740,651, filed Oct. 3, 2018, the disclosure of which is hereby incorporated herein by reference in its entirety.

FIELD OF THE DISCLOSURE

This application is related to monitoring of vital signals, and in particular to improved systems and methods for continuously monitoring a heart rate of a subject.

BACKGROUND

Heart disease remains the number one cause of death in the United States, according to recent statistics published by the American Heart Association. When it comes to early diagnosis and prevention of cardiovascular diseases, there are few measures more helpful than a subject's resting heart rate (HR). HR is also one of the most important vital sign parameters that can be used to inspect other potential health issues. For example, HR monitoring is important for elderly care, in-hospital monitoring, baby monitoring, and so on.

With the advancement of mobile technologies, increasing numbers of smart devices enter a consumer's daily life, including low-cost smart devices (e.g., smart phones, fitness trackers, smart wearable devices, Bluetooth electrocardiogram (ECG) sensors). Many of these devices can conveniently provide important physiological data, including HR. Not only can a normal resting HR vary from subject to subject, but if tracked over time it can also elicit some important data regarding a subject's heart health and fitness. For example, studies have shown that a rise in the resting HR of a subject can be linked to inadequate exercise, increased stress, obesity, and tobacco consumption. By changing the subject's life routine accordingly, the elevated HR can be lowered. In general, a low HR is desirable since it indicates that the heart is able to pump more blood with each heartbeat with greater efficiency.

SUMMARY

The present disclosure relates to using radar technology to measure the resting heart rate (HR) of a subject over time remotely. Various techniques exist to detect vital signs, and in particular a subject's heartbeat. In addition, various vital sign detection algorithms have been developed to improve the heartbeat detection performance. However, these algorithms' ability to monitor HR over time is not carefully studied in realistic situations.

In this regard, embodiments of the present disclosure include methods, systems, and devices for direct radio frequency (RF) signal processing for HR monitoring using ultra-wide band (UWB) impulse radar. A radar sensor is able to directly sample a received signal at RF which satisfies the Nyquist sampling rate, preserving a subject's vital sign information in the received signal. The vital sign information can be extracted directly from a raw RF signal and thus down conversion to a complex baseband is not required. The HR monitoring performance from the proposed direct RF signal processing technique provides an improvement in continuous HR monitoring as compared against existing methods using a complex baseband signal and/or other measurement techniques.

An exemplary embodiment relates to a method for continuously measuring HR. The method includes transmitting a series of radar impulses toward a subject and receiving an RF response signal corresponding to the series of radar impulses. The method further includes sampling the RF response signal to generate a sampled response signal at an RF band and measuring a HR of the subject from the sampled response signal at the RF band.

Another exemplary embodiment relates to a vital sign detection device. The device includes a radar transmitter configured to transmit a series of radar impulses and an RF receiver configured to receive an RF response signal to the series of radar impulses. The device further includes a processing circuit coupled to the RF receiver and configured to estimate a vital sign of a subject based on the RF response signal without converting the RF response signal to a baseband.

Another exemplary embodiment relates to a method of remotely monitoring a HR. The method includes transmitting a plurality of radar impulse signals to a subject over a distance between 0.5 meters (m) and 2.5 m and receiving an RF response signal to the plurality of radar impulse signals. The method further includes continuously monitoring a HR of the subject by analyzing the RF response signal in a spectral domain.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1:
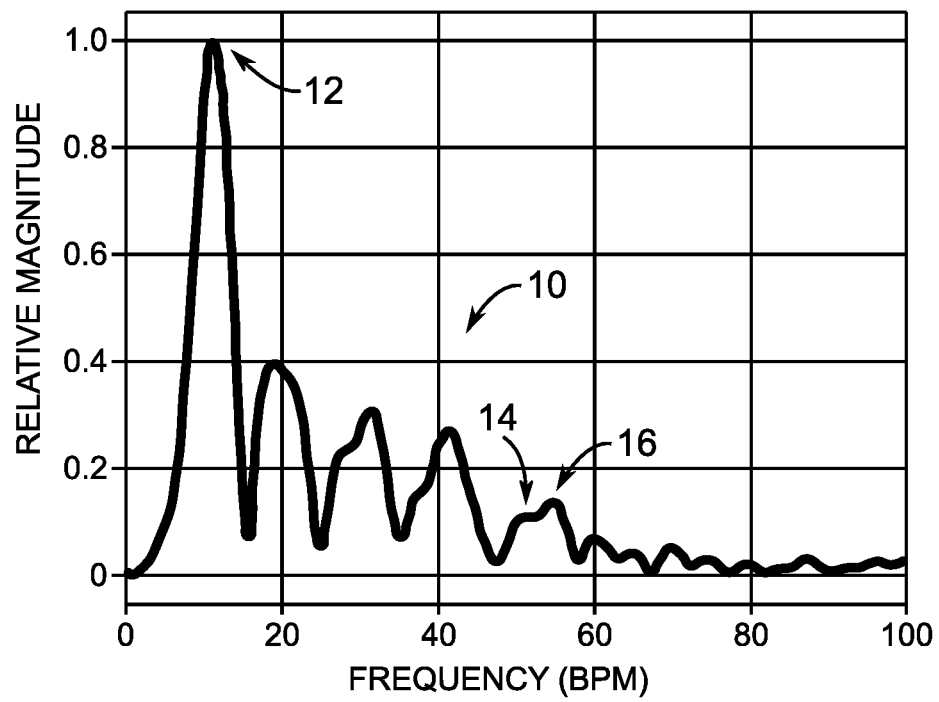
FIG. 1 is a graphical representation of spectral features of an exemplary radio frequency (RF) response signal, illustrating heart rate (HR) and respiration components.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The present disclosure relates to using radar technology to measure the resting heart rate (HR) of a subject over time remotely. Various techniques exist to detect vital signs, and in particular a subject's heartbeat. In addition, various vital sign detection algorithms have been developed to improve the heartbeat detection performance. However, these algorithms' ability to monitor HR over time is not carefully studied in realistic situations.

In this regard, embodiments of the present disclosure include methods, systems, and devices for direct radio frequency (RF) signal processing for HR monitoring using ultra-wide band (UWB) impulse radar. A radar sensor is able to directly sample a received signal at RF which satisfies the Nyquist sampling rate, preserving a subject's vital sign information in the received signal. The vital sign information can be extracted directly from a raw RF signal and thus down conversion to a complex baseband is not required. The HR monitoring performance from the proposed direct RF signal processing technique provides an improvement in continuous HR monitoring as compared against existing methods using a complex baseband signal and/or other measurement techniques.

I. Signal Model

Vital sign detection using UWB impulse radar can be characterized with a signal model. Under a conventional approach, a received RF response signal is directly sampled in RF and then digitally converted to a complex baseband. A fast-time sampling interval (range) is usually on the order of nanoseconds and an output slow-time sampling interval is on the order of micro-seconds. Under the signal model, $\tau$ denotes a fast sampling time and v is a transformed frequency component while t denotes a slow cross-range sample time and f is a corresponding Fourier domain component. The vital sign of a subject at a nominal distance $d_0$ can be modeled as a sum of two sine waves from respiratory and cardiac activities:

$$V(t) = d_0 + M_b \sin(2\pi f_b t) + M_h \sin(2\pi f_h t) \qquad \text{Eqn. 1}$$

where $M_b$ is an amplitude of respiratory activity, and $M_h$ is an amplitude of cardiac activity. Respiration and heartbeat frequencies are represented as $f_b$ and $f_h$.

In addition, the RF response signal received by an RF receiver in response to the UWB impulse radar can be modeled as a sum of a target response and a delayed, attenuated version of a transmitted pulse due to static environment:

$$r(t,\tau) = A_T p(\tau - \tau_D(t)) + \Sigma_i A_i p(\tau - \tau_i) \qquad \text{Eqn. 2}$$

where $p(t,\tau)$ is a generated short pulse, centered at a carrier frequency $F_c$. Magnitudes of the target response and multi-path components are denoted as $A_T$ and $A_i$, while $\tau_D(t)$ and $\tau_i$ are corresponding delays.

The RF response signal can further be modeled as:

$$r_o(t,\tau) = A_T p(\tau - \tau_D(t)) \qquad \text{Eqn. 3}$$

where the multi-path components due to static environment are eliminated by mean subtraction. Under a traditional approach, the received RF response signal is then down converted to a complex baseband and is represented as:

$$y(t, \tau) = r_o(t, \tau) e^{-j2\pi F_c \tau} \qquad \text{Eqn. 4}$$
$$= A_T p(\tau - \tau_D(t)) e^{-j2\pi F_c \tau}$$

II. Direct RF Signal Processing

In aspects disclosed herein, vital sign information can be directly extracted from the RF response signal in Eqn. 3 at the nominal target distance $d_0$, as follows:

$$\tau_D(t) = 2\frac{d_0 + V(t)}{c} = \tau_0 + 2\frac{V(t)}{c} \quad \text{Eqn. 5}$$

where c denotes the speed of light. A time-delay variation as a function of t due to chest movement is preserved in Eqn. 3. The Fourier analysis of Eqn. 3 generates a similar result for vital sign detection to the complex baseband signal processing result with the addition of some constant coefficient.

Through forward and backward Fourier transforms with respect to t and τ, the Fourier transform of Eqn. 3 with respect to t is given as:

$$Y^{RF}(f,\tau) = A_T \sum_{k=-\infty}^{\infty} \sum_{l=-\infty}^{\infty} \delta(f - kf_b - lf_h) \times \quad \text{Eqn. 6}$$
$$\int_{-\infty}^{\infty} dv \left[ P(v)e^{j2\pi v(\tau-\tau_0)} \times J_k\left(4\pi v \frac{M_b}{c}\right) J_l\left(4\pi v \frac{M_h}{c}\right) \right]$$

$$= A_T \sum_{k=-\infty}^{\infty} \sum_{l=-\infty}^{\infty} C_{k,l}(\tau) \delta(f - kf_b - lf_h) \quad \text{Eqn. 7}$$

where P(v) denotes a Fourier transform of the transmitted pulse p(τ) and $J_k(\cdot)$ denotes a Bessel function of the first kind. Therefore, the Fourier transform result of the received RF response signal in Eqn. 3 at the distance $d_0$ is given as:

$$|Y^{RF}(f,\tau_0)| = |A_T|\Sigma_{k=-\infty}^{\infty}\Sigma_{l=-\infty}^{\infty}|C_{k,l}(\tau_0)|\delta(f-kf_b-lf_h)$$
$$\geq |Y^{RF}(f,\tau)| \quad \text{Eqn. 8}$$

where an absolute value of a complex coefficient $C_{k,l}(\tau)$ achieves its maximum at the delay $\tau_0$ and $C_{k,l}(\tau)$ is given as, $$C_{k,l}(\tau) = \int_{-\infty}^{\infty} dv[P(v)e^{j2\pi v(\tau-\tau_0)} \times J_k(4\pi v M_b/c)J_l(4\pi v M_h/c)] \quad \text{Eqn. 9}$$

III. Vital Sign Higher-Order Spectral Features

FIG. 1 is a graphical representation of spectral features of an exemplary RF response signal 10, illustrating HR and respiration components. In an exemplary aspect, a harmonics-based HR estimation method can be used in the RF signal domain because the vital sign information and its associated higher-order spectral features are preserved in the direct RF sampled signal in Eqn. 3 above. The main idea of this harmonics-based HR estimation algorithm is briefly discussed here. In the spectrum domain, an exemplary embodiment looks for higher-order harmonics due to cardiac activity at a relatively higher frequency region, rather than looking for the fundamental heartbeat spectrum peak in the low frequency region.

Conventional methods use the fundamental heartbeat spectrum peak in an attempt to separate the heartbeat spectrum using a pre-defined bandpass filter with frequency limit (such as 0.7 hertz (Hz) to 1.6 Hz). This method fails when the subject's resting HR is low and close to the respiration harmonics region, especially the lower-order respiration harmonics. For example, FIG. 1 illustrates a respiration peak 12 (at approximately 11 beats per minute (BPM)) and a fundamental heartbeat peak 14 (at approximately 55 BPM) in the exemplary RF response signal 10. As further illustrated, a lower-order respiration harmonic 16 (e.g., the fifth respiration harmonic 16) can be stronger than the fundamental heartbeat peak 14. Even worse, in some cases the fundamental heartbeat peak 14 and the $2^{nd}$ or the $3^{rd}$ respiration harmonics might collocate in the spectral domain. Due to these facts, this approach cannot provide reliable continuous measurement.

In contrast, aspects of the present disclosure estimate the HR based on its higher-order harmonics since they are separated by a fundamental heartbeat frequency (e.g., the frequency at the fundamental heartbeat peak 14). The higher-order harmonics are obtained through a harmonics bandpass filter (e.g., 1.5 Hz to 4 Hz), where the upper limit is trivial and the lower limit is determined by the HR statistics of human subjects (e.g., the normal resting adult HR). As illustrated in FIG. 1, when the fundamental heartbeat peak 14 collocates with the lower-order respiration harmonic 16, the HR cannot be automatically separated without an external reference signal and thus cannot be estimated with confidence.

TABLE I

VITAL SIGN SIMULATION PARAMETERS

| Chest Motion | Resp. Rate | Heartbeat Motion | Heart Rate |
| --- | --- | --- | --- |
| 0~5 mm | 15 BPM | 0.08 mm | 70 BPM |

IV. Respiration-Free Demonstration

In this section, a quantitative analysis compares the strength of the $2^{nd}$-order harmonics of a heartbeat and its nearby possible competitors in the spectral domain, such as higher-order respiration harmonics and inter-modulations. To perform the following numerical evaluation, some realistic numbers are considered, as summarized in Table I.

Figure 2:
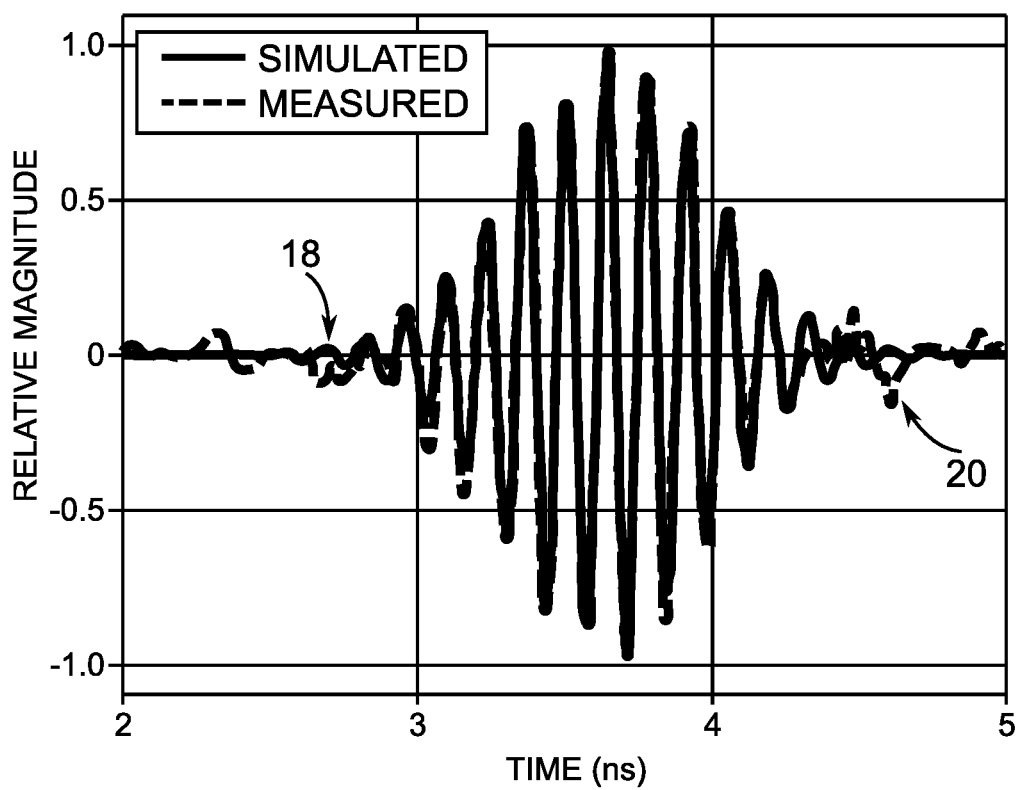
FIG. 2 is a graphical representation of a synthesized ultra-wide band (UWB) pulse and a measured UWB pulse transmitted by a radar transmitter.

A more accurate evaluation is performed to calculate the harmonics strength. Instead of using mean value approximation to evaluate Eqn. 9, the actual transmitted waveform has been taken into consideration. In this regard, FIG. 2 is a graphical representation of a synthesized UWB pulse 18 and a measured UWB pulse 20 transmitted by a radar transmitter. The synthesized UWB pulse 18 is modeled as a cosine wave with a Gaussian envelope:

$$p(\tau) = p_0(\tau)\cos(2\pi F_c \tau) \quad \text{Eqn. 10}$$
$$= V_{Tx} e^{-\frac{\tau^2}{2\sigma^2}} \cos(2\pi F_c \tau)$$

where $V_{Tx}$ is a pulse amplitude of the Gaussian pulse envelope $p_0(\tau)$ and the Gaussian parameter determines the −10 dB bandwidth, $$\sigma = \frac{1}{2\pi(BW/2)\sqrt{\log_{10}(e)}} \quad \text{Eqn. 11}$$

Given the radar system parameters, carrier frequency $F_c=7.3$ GHz and operating bandwidth BW=1.4 GHz, the waveform of the synthesized UWB pulse 18 corresponds to the measured UWB pulse 20 as seen in FIG. 2.

Figure 3:
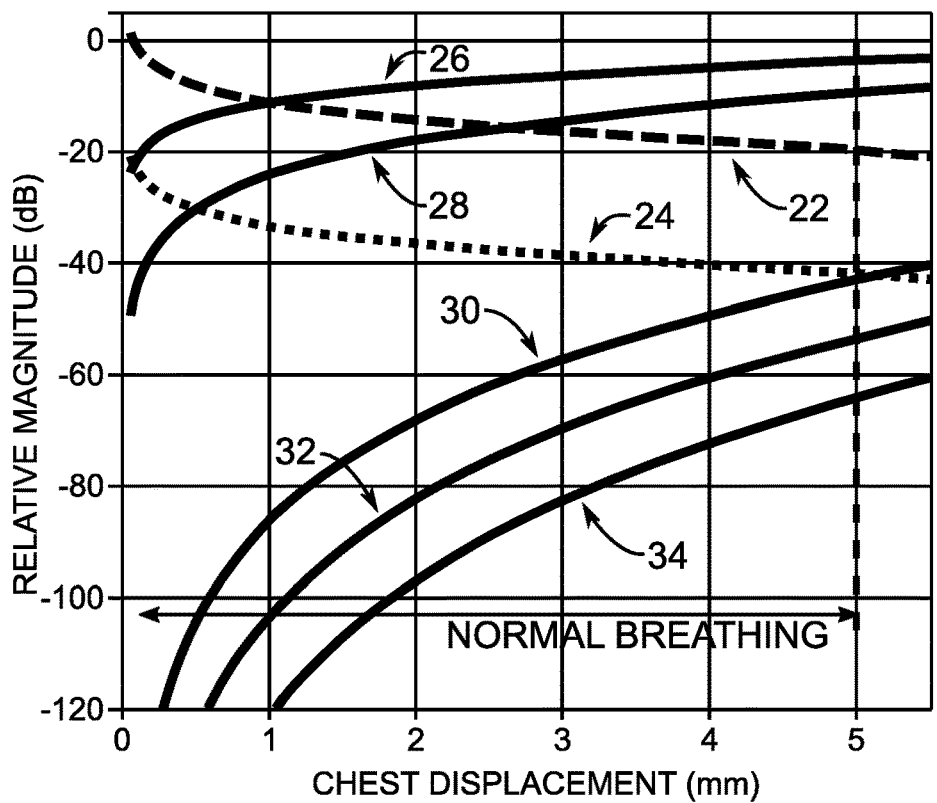
FIG. 3 is a graphical representation of heartbeat harmonics and respiration harmonics as a function of chest movement, illustrating an exemplary approach for extracting HR measurements from the RF response signal.

FIG. 3 is a graphical representation of heartbeat harmonics 22, 24 and respiration harmonics 26, 28, 30, 32, 34 as a function of chest movement, illustrating an exemplary approach for extracting HR measurements from the RF response signal. This approach begins by comparing the strength of the respiration harmonics 26, 28, 30, 32, 34 to the $2^{nd}$-order heartbeat harmonic 24. Then the strength of the higher-order inter-modulations is compared to the heartbeat harmonics of interest.

The harmonics strength is obtained by evaluating the integral in Eqn. 9 using the waveform of the synthesized UWB pulse 18 at −10 dB bandwidth with $\tau=\tau_0$. Given a fundamental HR of 70 BPM, the $2^{nd}$-order heartbeat harmonic 24 (140 BPM) is competing against an $8^{th}$-order respiration harmonic 30, a $9^{th}$-order respiration harmonic 32, and a $10^{th}$-order respiration harmonic 34, ranging from 120 to 150 BPM. Only the higher-order respiration harmonics 30, 32, 34 that are close to the $2^{nd}$-order heartbeat harmonic 24 are considered, otherwise they can be easily filtered out.

For normal respiratory activity, the $2^{nd}$-order heartbeat harmonic 24 is much stronger than the $8^{th}$-order respiration harmonic 30, the $9^{th}$-order respiration harmonic 32, and the $10^{th}$-order respiration harmonic 34, as illustrated in FIG. 3. For different chest displacement, the fundamental heartbeat experiences interference from lower-order harmonics of the respiration (e.g., a $2^{nd}$-order respiration harmonic 26). In general, the higher-order harmonics with an order number $m=k+l\geq 4$, where k and l are from $C_{k,l}^B(\tau_0)$, cannot be easily observed due to the weak vital sign signal and the background noise. The main challenge of monitoring the fundamental heartbeat over time is due to the spurious spectrum peaks such as the $2^{nd}$-order respiration harmonic 26 or a $3^{rd}$-order respiration harmonic 28. Fortunately, they are spectrally further away from the frequency of the $2^{nd}$-order heartbeat harmonic 24.

Figure 4:
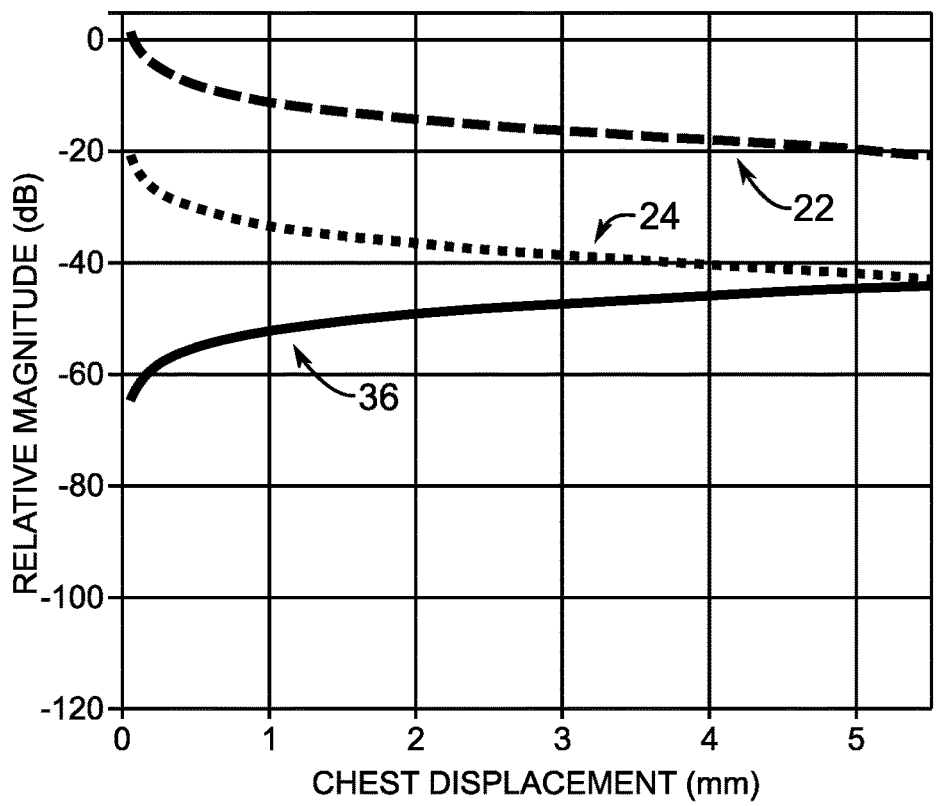
FIG. 4 illustrates relative strengths of $2^{nd}$-order heartbeat harmonics vs. inter-modulations as a function of chest movement.

FIG. 4 is a graphical representation of heartbeat harmonics 22, 24 and inter-modulations 36 as a function of chest movement. The strength of the higher-order inter-modulations 36 are compared against the strength of the $2^{nd}$-order heartbeat harmonic 24. The associated inter-modulations 36 close to 140 BPM are $C_{k=-1,l=2}^B(\tau_0)$ and $C_{k=1,l=2}^B(\tau_0)$. Only the order numbers of the inter-modulations 36 $m\leq 3$ are considered. Under normal breathing, the $2^{nd}$-order heartbeat harmonic 24 is the dominant spectral component in this frequency region. Therefore, locating the $2^{nd}$-order heartbeat harmonic 24 becomes a respiration-interference free task.

V. Issues of Phase-Based Approach

A phase-based estimation approach is widely used for vital sign detection. The main motivation of this traditional approach is that the phase variation is directly related to vital sign information. Theoretically, in the spectral domain, two peaks will be observed: the larger one is due to respiration and the smaller one is heartbeat frequency. To obtain the phase information, a fast-time Fourier transform is performed on the complex baseband signal in Eqn. 4:

$$Y^B(t,v) = A_T P(v+F_c) e^{-j(v+F_c)\pi D(t)}$$

$$Y^B(t,0) = A_T P(v+F_c) e^{-j(F_c)\pi D(t)} \quad \text{Eqn. 12}$$

where in order to evaluate $Y^B(t, v)$, v is set to 0, corresponding to summing over the range bins near the distance $d_0$. Since $A_T$ is a real constant and $P(F_c)$ is a complex constant only contributing a constant phase residual, the desired phase information $T_D(t)$ is preserved in the exponential term $Y^B(t, 0) = I(t)+jQ(t)$.

In a real system, phase noise is inevitable and a phase calibration procedure is required to correctly extract phase information. Since the down conversion is performed in a digital domain, the major source of phase noise is presented in direct current (DC) as $D_I$ and $D_Q$ in an in-phase/quadrature (I/Q) channel. Let $\dot{I}(t)$ and $\dot{Q}(t)$ denote the distorted I/Q data, $$\dot{\phi}(t) = \text{unwrapping}\left\{A\tan\left(\frac{\dot{Q}(t)}{\dot{I}(t)}\right)\right\} \quad \text{Eqn. 13}$$

$$= \text{unwrapping}\left\{A\tan\left(\frac{A_0\sin(4\pi V(t)/\lambda + \varphi_0) + D_Q}{A_0\cos(4\pi V(t)/\lambda + \varphi_0) + D_I}\right)\right\}$$

$$\rightarrow \frac{4\pi V(t)}{\lambda} + \varphi_0$$

where $A_0$ and $\phi_0$ are the nominal amplitude and the constant phase residual. If the DC-offset can be perfectly corrected, the final expression is the desired phase information. A phase error calibration procedure is often implemented, which has been shown to be one of the most accurate center tracking algorithms.

Figure 5:
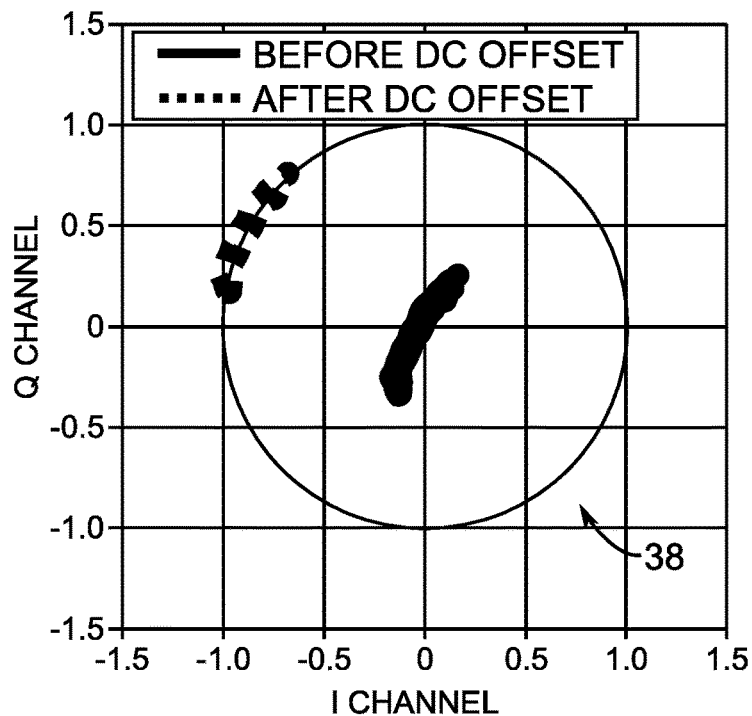
FIG. 5 is an in-phase/quadrature (I/Q) data constellation plot from a normal breathing subject but with a controlled regular breathing pattern before and after a direct current (DC)-offset correction under a traditional phase-based approach.

FIG. 5 is an I/Q data constellation plot 38 from a normal breathing subject but with a controlled regular breathing pattern before and after a DC-offset correction under the traditional phase-based approach. The effectiveness of the phase-based approach with DC-offset calibration has been demonstrated, but here the challenge of correctly applying this method in a realistic situation is explained. For example, it must be determined which of these data points need to be corrected at every processing window. Ideally, the data points corresponding to the same micro-motion (meaning that they belong to the same phase trajectory in the I/Q data constellation plot 38 of FIG. 5) should be corrected at each processing window.

Figure 6:
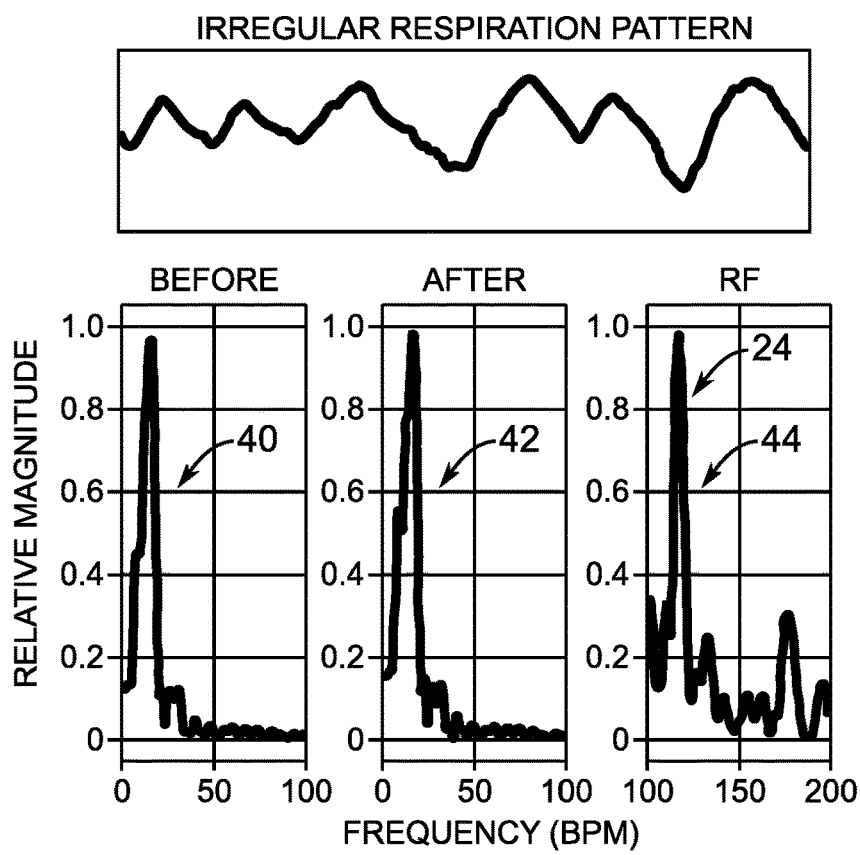
FIG. 6 illustrates spectrum results from the phase-based approach before DC-offset correction, the phase-based approach after DC-offset correction, and a direct RF estimation approach according to embodiments of the present disclosure.

In reality, respiratory activity, the stronger motion in the vital sign, can be quite different from breath to breath as seen in FIG. 6 and thus the calibration should be performed on a similar respiration pattern. FIG. 6 illustrates spectrum results from a phase-based approach before DC-offset correction 40, a phase-based approach after DC-offset correction 42, and a direct RF estimation approach 44 according to embodiments of the present disclosure. An automatic approach should be developed to perform this task.

Most practitioners apply the phase calibration method on fixed length data points, like 15-second or 20-second of data points, implicitly assuming that the respiratory activity is a stationary process. On the contrary, it is a time-varying and non-stationary process even for a resting subject. Without taking these facts into consideration, the phase calibration can introduce spectrum distortion as shown in the phase-based approaches 40, 42 of FIG. 6 (generated from a 20-second dataset containing irregular respiration pattern acquired from normal breathing subject). However, in this example the proposed direct RF estimation approach 44 can accurately recover the fundamental HR from the $2^{nd}$-order heartbeat harmonic 24: 117.8/2≈59 BPM. Additionally, the phase-based approaches 40, 42 are iterative and require much more computation than the proposed direct RF estimation approach 44.

VI. Proposed Method and System

Figure 7A:
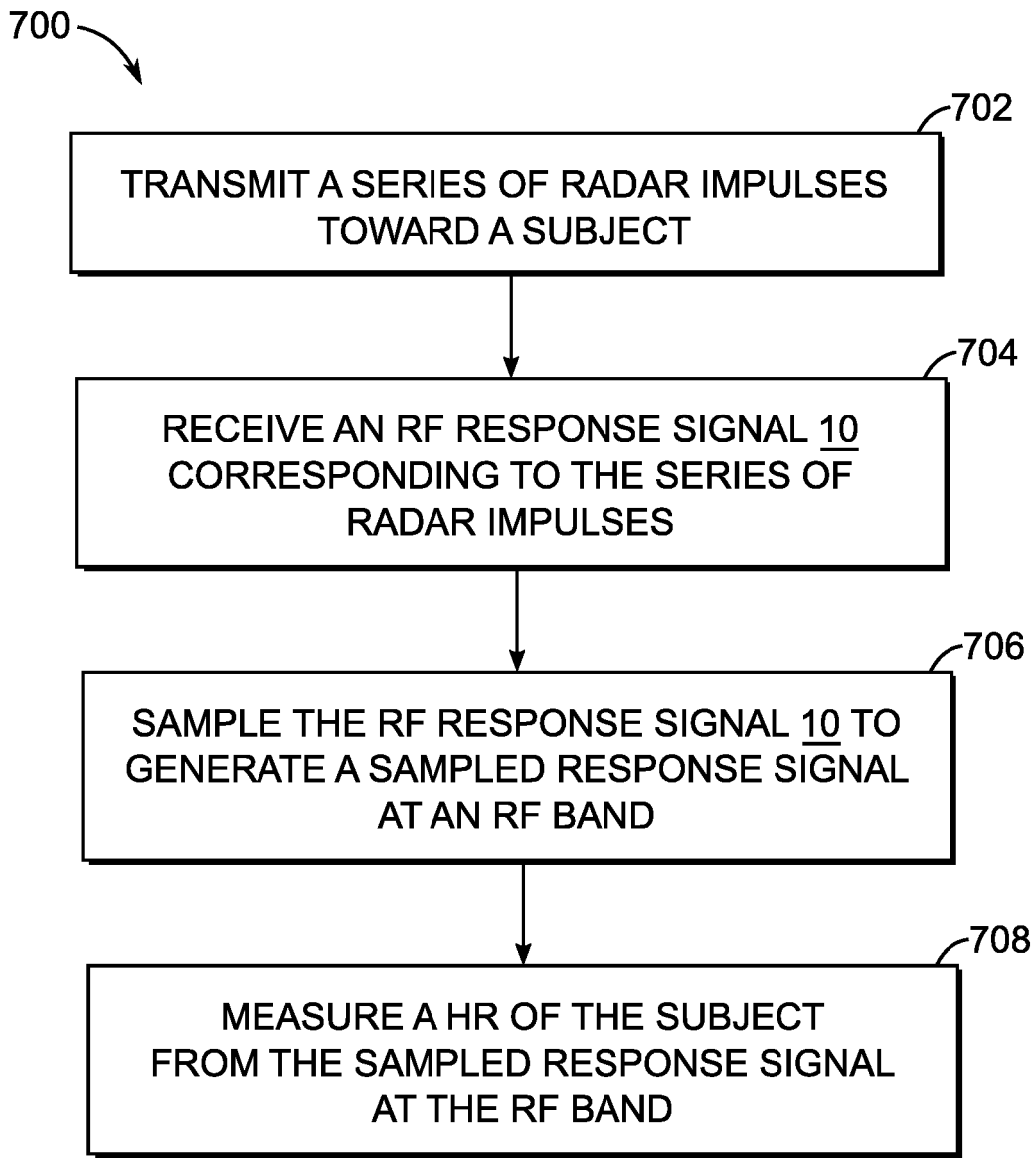
FIG. 7A is a flow diagram illustrating an exemplary method for continuously measuring HR.

FIG. 7A is a flow diagram illustrating an exemplary method 700 for continuously measuring HR. The method includes operation 702 with transmitting a series of radar impulses toward a subject. In an exemplary aspect, a radar transmitter transmits the synthesized UWB pulse 18. The method 700 further includes operation 704 with receiving the RF response signal 10 corresponding to the series of radar impulses. The method 700 further includes operation 706 with sampling the RF response signal 10 to generate a sampled response signal at an RF band. The method 700 further includes operation 708 with measuring a HR of the subject from the sampled response signal at the RF band.

Figure 7B:
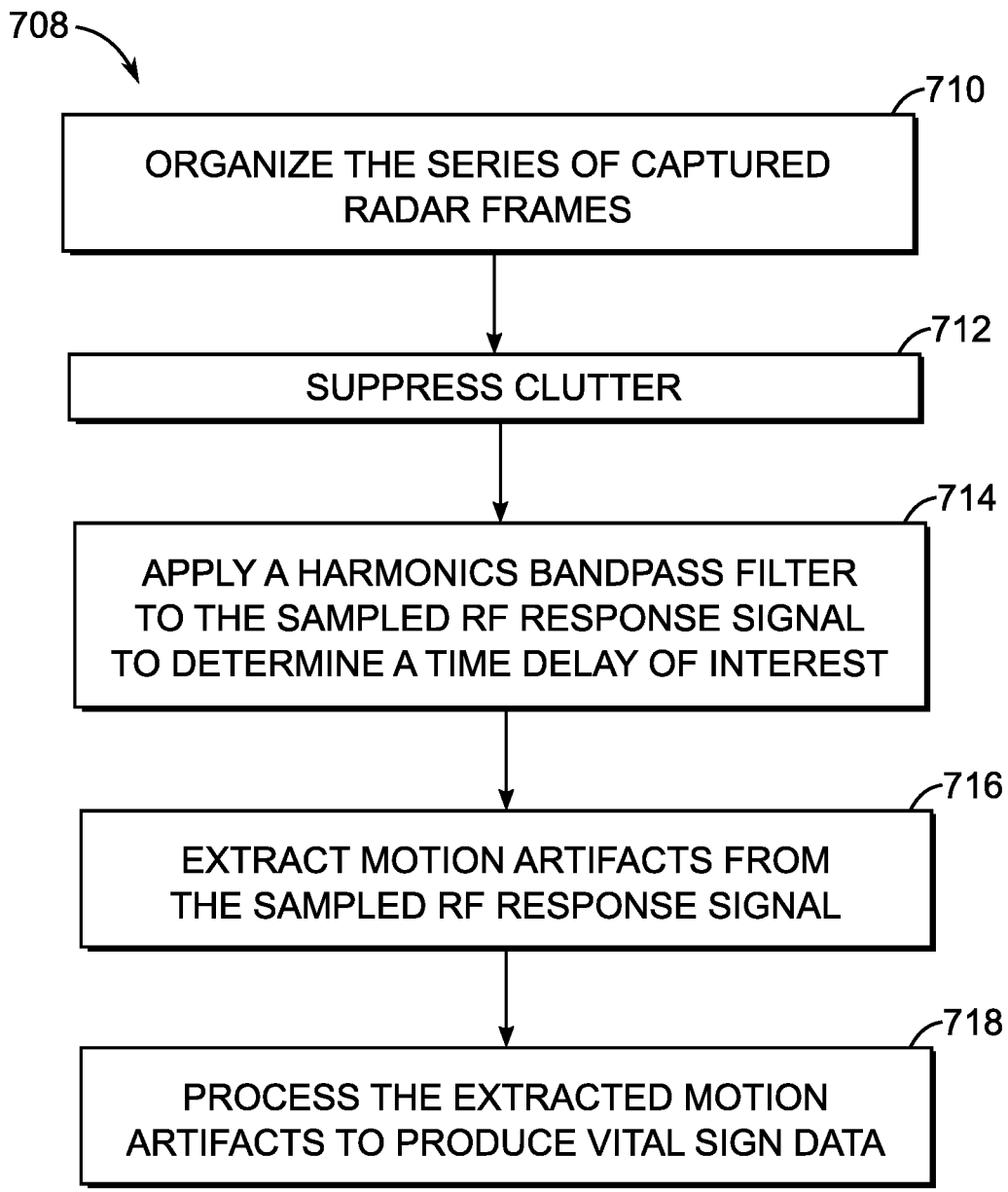
FIG. 7B is a flow diagram illustrating details of the direct RF signal processing approach for measuring the HR of the subject in the method of FIG. 7A.

FIG. 7B is a flow diagram illustrating details of the direct RF signal processing approach for measuring the HR (operation 708) of the subject in the method 700 of FIG. 7A. In an exemplary aspect, the RF response signal 10 includes a series of captured radar frames. In operation 710, after sampling the RF response signal 10, the series of captured radar frames is organized.

Next, in operation 712, clutter suppression is performed on the acquired mixed data to remove static background. The clutter suppression may be realized by high-pass filtering. In some applications, the clutter suppression may be omitted. In operation 714, a harmonics bandpass filter is applied to the sampled RF response signal to determine a time delay of interest for the subject. The time delay of interest refers to a time delay range at one or more impulse responses (e.g., each impulse response) in which a portion of the sampled RF response signal contains the highest energy. In some examples, the time delay of interest also indicates a distance between the subject and the radar transmitter.

While remaining in the RF domain, in operation 716, motion artifacts are extracted from the sampled RF response signal. The motion artifacts are extracted by measuring changes in amplitude of the sampled RF response signal at each of the radar frames at the time delay of interest. The extracted motion artifacts can include the respiration component and the heartbeat component, as modeled above. In operation 718, the extracted motion artifacts are processed to produce vital sign data. As further described above, processing the extracted motion artifacts includes locating the $2^{nd}$-order heartbeat harmonic 24 (and/or other higher-order harmonics) of the subject.

Although the operations of FIGS. 7A and 7B are illustrated in a series, this is for illustrative purposes and the operations are not necessarily order dependent. Some operations may be performed in a different order than that presented. Further, processes within the scope of this disclosure may include fewer or more steps than those illustrated in FIGS. 7A and 7B.

Figure 8:
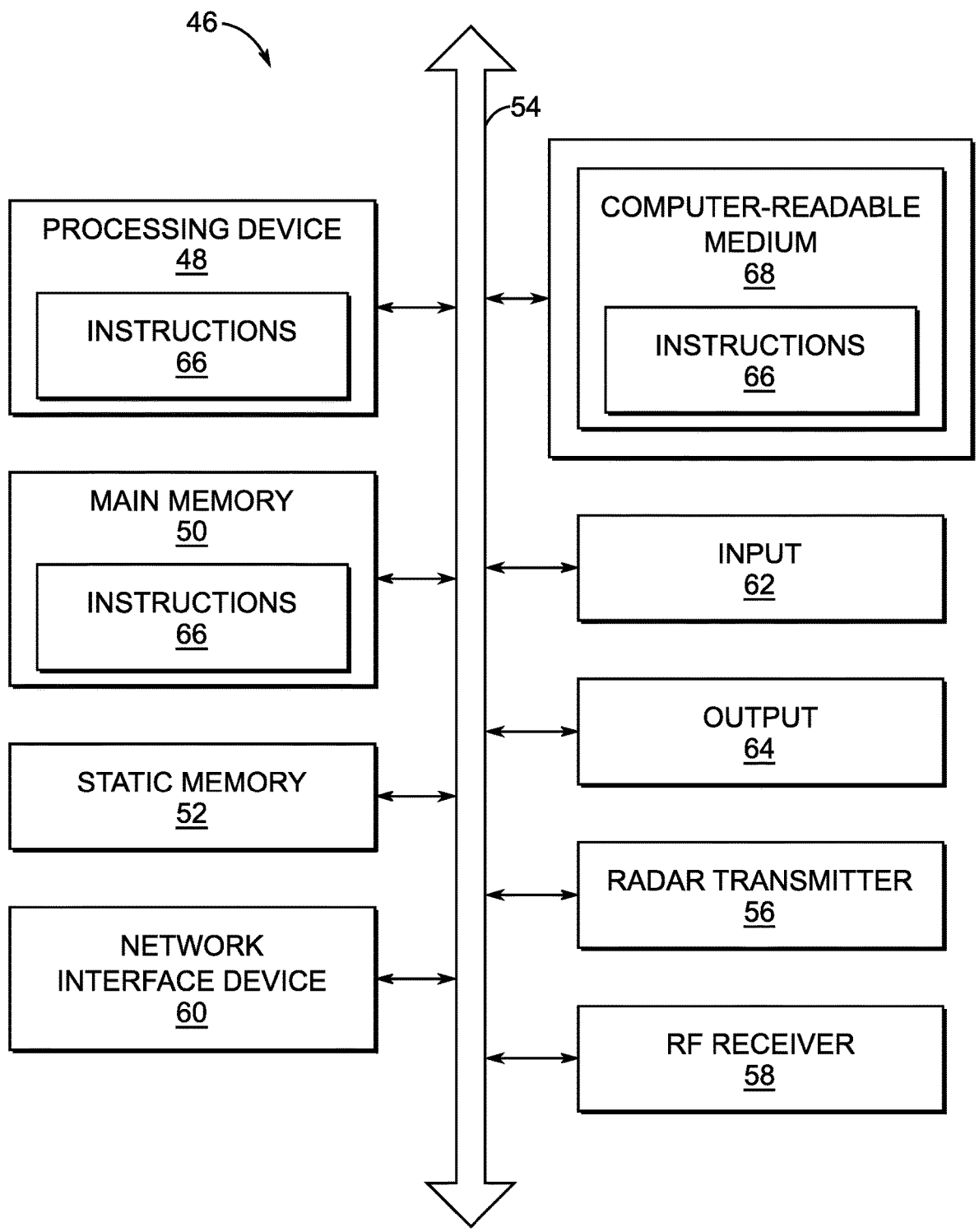
FIG. 8 is a schematic diagram of an exemplary vital sign detection device applying the direct RF signal processing approach of the present disclosure.

FIG. 8 is a schematic diagram of an exemplary vital sign detection device 46 applying the direct RF signal processing approach of the present disclosure. In this regard, the vital sign detection device 46 may be a circuit or circuits included in an electronic board card, such as, a printed circuit board (PCB), a server, a personal computer, a desktop computer, a laptop computer, an array of computers, a personal digital assistant (PDA), a computing pad, a mobile device, or any other device, and may represent, for example, a server or a user's computer.

The vital sign detection device 46 in this embodiment includes a processing device 48 or processor, a main memory 50 (e.g., read-only memory (ROM), flash memory, dynamic random access memory (DRAM), such as synchronous DRAM (SDRAM), etc.), and a static memory 52 (e.g., flash memory, SRAM, etc.), which may communicate with each other via a data bus 54. Alternatively, the processing device 48 may be connected to the main memory 50 and/or the static memory 52 directly or via some other connectivity means. In an exemplary aspect, the processing device 48 may be used to perform any of the methods or functions described above, such as measuring and/or monitoring the HR or other vital signs of a subject.

The processing device 48 represents one or more general-purpose processing devices, such as a microprocessor, central processing unit (CPU), or the like. More particularly, the processing device 48 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 48 is configured to execute processing logic in instructions for performing the operations and steps discussed herein.

The various illustrative logical blocks, modules, and circuits described in connection with the embodiments disclosed herein may be implemented or performed with the processing device 48, which may be a field programmable gate array (FPGA), a digital signal processor (DSP), an application-specific integrated circuit (ASIC), or other programmable logic device, a discrete gate or transistor logic, discrete hardware components, or any combination thereof designed to perform the functions described herein. Furthermore, the processing device 48 may be a microprocessor, or may be any conventional processor, controller, microcontroller, or state machine. The processing device 48 may also be implemented as a combination of computing devices (e.g., a combination of a DSP and a microprocessor, a plurality of microprocessors, one or more microprocessors in conjunction with a DSP core, or any other such configuration).

The vital sign detection device 46 further includes a radar transmitter 56 configured to transmit a series of radar impulses. Each of the series of radar impulses may be similar to the synthesized UWB pulse 18 described above. The vital sign detection device 48 further includes an RF receiver 58 configured to receive the RF response signal 10 to the series of radar impulses, which are processed by the processing device 48 as described above. In some examples, the radar transmitter 56 and the RF receiver 58 can be separate components of the vital sign detection device 46. In other examples, the radar transmitter 56 and the RF receiver 58 can be implemented in one component.

The vital sign detection device 46 may further include a network interface device 60. The vital sign detection device 46 also may or may not include an input 62, configured to receive input and selections to be communicated to the vital sign detection device 46 when executing instructions. The vital sign detection device 46 also may or may not include an output 64, including but not limited to a display, a video display unit (e.g., a liquid crystal display (LCD) or a cathode ray tube (CRT)), an alphanumeric input device (e.g., a keyboard), and/or a cursor control device (e.g., a mouse).

The vital sign detection device 46 may or may not include a data storage device that includes instructions 66 stored in a computer-readable medium 68. The instructions 66 may also reside, completely or at least partially, within the main memory 50 and/or within the processing device 48 during execution thereof by the vital sign detection device 46, the main memory 50, and the processing device 48 also constituting computer-readable medium. The instructions 66 may further be transmitted or received via the network interface device 60.

While the computer-readable medium 68 is shown in an exemplary embodiment to be a single medium, the term "computer-readable medium" should be taken to include a single medium or multiple media (e.g., a centralized or distributed database, and/or associated caches and servers) that store the one or more sets of instructions 66. The term "computer-readable medium" shall also be taken to include any medium that is capable of storing, encoding, or carrying a set of instructions for execution by the processing device and that causes the processing device to perform any one or more of the methodologies of the embodiments disclosed herein. The term "computer-readable medium" shall accordingly be taken to include, but not be limited to, solid-state memories, optical medium, and magnetic medium.

VII. Performance Demonstration

Figure 9:
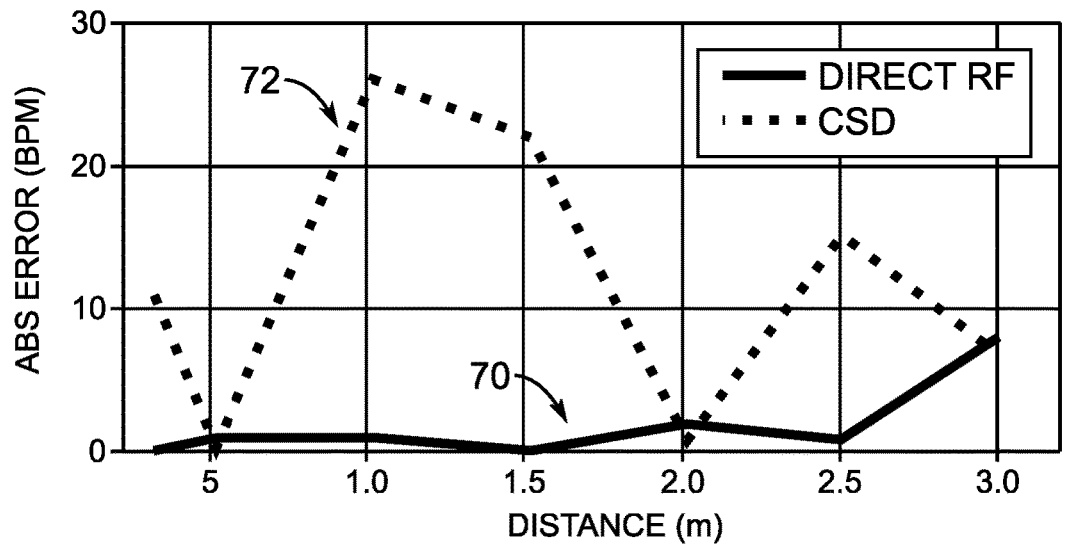
FIG. 9 is a graphical representation of continuous HR monitoring performance at different ranges.

In this section, experimental results are provided. FIG. 9 is a graphical representation of continuous HR monitoring performance at different ranges. In this example, seven measurements are captured ranging from 0.3 m to 3 m. A direct RF estimation approach 70 using the harmonics-based HR estimation algorithm described above can correctly detect the HR up to 2.5 m with a maximum error of 2 BPM at 2 m. A conventional complex signal demodulation (CSD) approach 72 in the complex baseband signal domain does not provide consistent estimates and results in large errors due to strong respiration harmonics.

Figure 10:
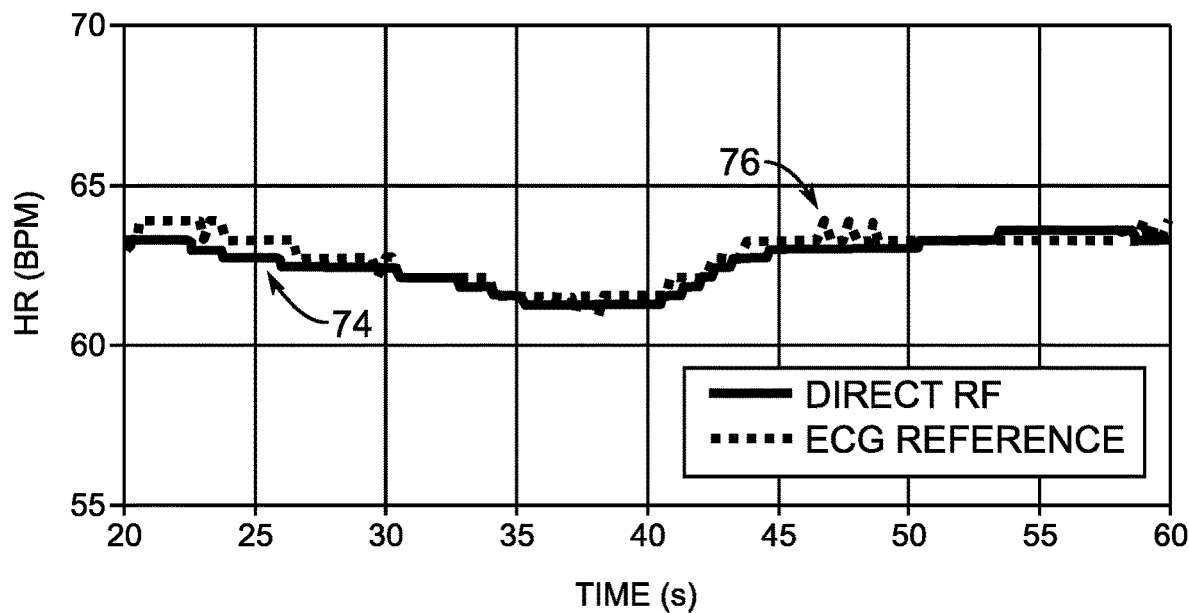
FIG. 10 is a graphical representation of the direct RF estimation approach compared with a reference electrocardiogram (ECG).

FIG. 10 is a graphical representation of the direct RF estimation approach compared with a reference electrocardiogram (ECG). This example demonstrates the accuracy of a continuous measurement performance 74 of the direct RF estimation approach by comparing against a standard ECG reference signal 76. During the entire recording, the radar estimates are consistent with the ECG reference signal 76 and the estimation error is well within 1 BPM.

In this disclosure, it has been shown that the directly sampled RF signal preserves the vital sign information. The disclosure further presents a harmonics-based HR estimation algorithm in the RF domain. As for heartbeat identifiability in the spectral domain, the fundamental heartbeat is interference limited and the heartbeat harmonics are signal-to-noise ratio limited. The first issue is a much more challenging task as discussed herein. The second issue can be solved by coherently combining a relatively large number of pulses to achieve the desired processing gain since the pulse repetition rate can be much higher than 1 MHz.

Those skilled in the art will recognize improvements and modifications to the preferred embodiments of the present disclosure. All such improvements and modifications are considered within the scope of the concepts disclosed herein and the claims that follow.

The invention claimed is:

1. A method for continuously measuring heart rate, comprising:
    transmitting a series of radar impulses toward a subject;
    receiving a radio frequency (RF) response signal corresponding to the series of radar impulses;
    sampling the RF response signal to generate a sampled response signal at an RF band, wherein the RF response signal comprises a plurality of captured radar frames;
    applying a harmonics bandpass filter to the sampled response signal to identify a time delay of interest in the plurality of captured radar frames;
    measuring a heart rate of the subject from the sampled response signal at the RF band and without a baseband conversion.

2. The method of claim 1, wherein the RF response signal comprises a plurality of captured radar frames.

3. The method of claim 1, wherein measuring the heart rate comprises measuring changes in amplitude of the sampled response signal at each of the plurality of captured radar frames at the time delay of interest.

4. The method of claim 1, wherein the harmonics bandpass filter is between 1.5 hertz (Hz) and 4 Hz.

5. The method of claim 1, wherein the series of radar impulses comprises ultra-wide band (UWB) radar impulses.

6. The method of claim 1, wherein measuring the heart rate comprises locating second order harmonics of a heartbeat of the subject.

7. The method of claim 6, wherein the locating the second order harmonics of the heartbeat removes respiration interference from the sampled response signal.

8. The method of claim 1, wherein the series of radar impulses is transmitted at a distance of between 1 meter (m) and 2.5 m from the subject.

9. A vital sign detection device, comprising:
    a radar transmitter configured to transmit a series of radar impulses;
    a radio-frequency (RF) receiver configured to receive an RF response signal from the series of radar impulses; and
    a processing circuit coupled to the RF receiver and configured to estimate a vital sign of a subject based on the RF response signal without converting the RF response signal to a baseband, wherein the processing circuit is further configured to apply harmonics bandpass filtering to the sampled response signal to identify a time delay of interest in the RF response signal based on an output of the harmonics bandpass filtering.

10. The vital sign detection device of claim 9, wherein:
    the radar transmitter comprises an ultra-wide band (UWB) radar transmitter; and
    each impulse of the series of radar impulses comprises a bandwidth between 1.0 gigahertz (GHz) and 2.0 GHz.

11. The vital sign detection device of claim 9, wherein the processing circuit is configured to estimate the vital sign of the subject by:
    sampling the RF response signal to generate a sampled response signal at an RF band; and
    measuring a heart rate of the subject from the sampled response signal at the RF band.

12. The vital sign detection device of claim 9, wherein the processing circuit is configured to estimate the vital sign by measuring changes in amplitude of the RF response signal at the time delay of interest.

13. The vital sign detection device of claim 9, wherein the processing circuit is configured to estimate the vital sign comprising a heart rate of the subject after removing respiration motion artifacts from the RF response signal.

14. The vital sign detection device of claim 9, wherein the RF response signal comprises a plurality of captured radar frames, and the time delay of interest is identified in the plurality of captured radar frames.

15. The vital sign detection device of claim 9, wherein the harmonics bandpass filtering is between 1.5 hertz (Hz) and 4 Hz.

16. A method of remotely monitoring a heart rate, comprising:
    transmitting a plurality of radar impulse signals to a subject over a distance between 0.5 meters (m) and 2.5 m;
    receiving a radio frequency (RF) response signal from the plurality of radar impulse signals;
    applying a harmonics bandpass filter to the RF response signal and measuring changes in amplitude of the RF response signal over the plurality of radar impulse signals; and
    continuously monitoring a heart rate of the subject by analyzing the RF response signal in a spectral domain, wherein the heart rate is measured from the RF response signal without a baseband conversion.

17. The method of claim 16, wherein the harmonics bandpass filter is between 1.5 hertz (Hz) and 4 Hz.

* * * * *